(12) United States Patent
Minowa et al.

(10) Patent No.: US 7,772,426 B2
(45) Date of Patent: Aug. 10, 2010

(54) METHOD FOR PRODUCING L-2-AMINO-4-(HYDROXYMETHYL-PHOSPHINYL)-BUTANOIC ACID

(75) Inventors: Nobuto Minowa, Kanagawa (JP); Nozomu Nakanishi, Kanagawa (JP); Masaaki Mitomi, Kanagawa (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 287 days.

(21) Appl. No.: 11/909,839

(22) PCT Filed: Mar. 28, 2006

(86) PCT No.: PCT/JP2006/306219

§ 371 (c)(1),
(2), (4) Date: Sep. 27, 2007

(87) PCT Pub. No.: WO2006/104120

PCT Pub. Date: Oct. 5, 2006

(65) Prior Publication Data

US 2008/0146837 A1    Jun. 19, 2008

(30) Foreign Application Priority Data

Mar. 29, 2005   (JP) .............................. 2005-093949

(51) Int. Cl.
C07C 227/32   (2006.01)
(52) U.S. Cl. .................. 562/443; 562/575; 560/38; 560/155
(58) Field of Classification Search .................... 560/38, 560/155; 562/443, 575
See application file for complete search history.

(56) References Cited

U.S. PATENT DOCUMENTS

| | | | |
|---|---|---|---|
| 4,168,963 A | 9/1979 | Rupp et al. | |
| 4,499,027 A | 2/1985 | Minowa et al. | |
| 4,777,279 A | 10/1988 | Zeiss | |
| 4,922,006 A | 5/1990 | Zeiss | |
| 6,337,406 B1 | 1/2002 | Zhang | |
| 6,686,181 B1 | 2/2004 | Bartsch | |
| 6,727,377 B2 | 4/2004 | Zhang | |
| 6,936,444 B1 | 8/2005 | Bartsch | |
| 6,946,569 B2 | 9/2005 | Zhang | |
| 7,105,702 B2 | 9/2006 | Zhang et al. | |
| 7,153,809 B2 | 12/2006 | Zhang et al. | |
| 7,169,953 B2 | 1/2007 | Zhang et al. | |

FOREIGN PATENT DOCUMENTS

| | | |
|---|---|---|
| JP | 52-139727 | 11/1977 |
| JP | 55-000025 | 1/1980 |
| JP | 59-219297 | 12/1984 |
| JP | 62-132891 | 6/1987 |
| JP | 62-226993 | 10/1987 |
| JP | 2002-523419 | 7/2002 |
| JP | 2003-505031 | 2/2003 |
| JP | 2003-528572 | 9/2003 |
| WO | 03/040149 | 5/2003 |
| WO | 03/042135 | 5/2003 |
| WO | 2004-035594 | 4/2004 |

OTHER PUBLICATIONS

Chemical Society of Japan, "Jikken Kagaku Koza (Course of Study of Experimental Chemical) 4th ed.", Organic metallic complex, 18, 339-344 (1991).

(Continued)

*Primary Examiner*—Peter G O'Sullivan
(74) *Attorney, Agent, or Firm*—Greenblum & Bernstein, P.L.C.

(57) ABSTRACT

Disclosed is a method for efficiently and highly selectively producing L-2-amino-4-(hydroxymethylphosphinyl)-butanoic acid, which is useful as a herbicide, through a catalytic asymmetric synthesis reaction. Specifically disclosed is a method for producing L-2-amino-4-(hydroxymethylphosphinyl)-butanoic acid which is characterized in that a dehydroamino acid is subjected to an asymmetric hydrogenation by using a rhodium catalyst represented by the formula (2) below and having an optically active cyclic phosphine ligand, and then the resulting product is subjected to hydrolysis:

$$[Rh(R^4)(L)]X \qquad (2)$$

[where $R^4$ represents 1,5-cyclooctadien or norbornadien; L represents a substance represented by the following formula (6):

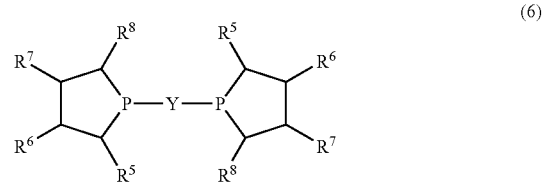

(6)

(wherein $R^5$ and $R^8$ respectively represent a $C_{1-4}$ alkyl group; $R^6$ and $R^7$ respectively represent hydrogen atom or hydroxyl group; and Y represents a group selected from groups represented by the following formula (7):

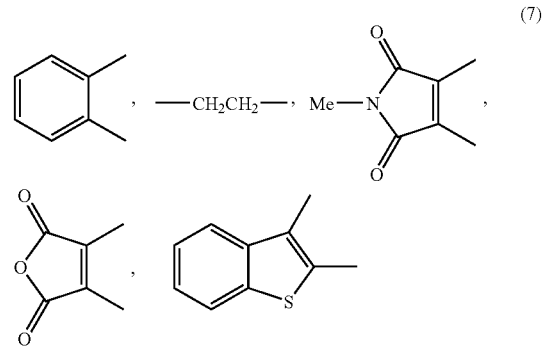

(7)

(where Me represents methyl group)).].

18 Claims, No Drawings

OTHER PUBLICATIONS

English Language Abstract of JP 55-000025, (1980).
English Language Abstract of JP 59-219297, (1984).
English Language Abstract of WO 2004/035594, (2004).
J. Singh et al. "Efficient Asymmetric Synthesis of the Vasopeptidase Inhibitor BMS-189921", Organic Letters, 2003, vol. 5, No. 17, 3155-3158.
H. -J. Zeiss et al. "An Efficient Asymmetric Synthesis of Both Enantiomers of Phosphinothricin", Tetrahedron Letters, vol. 28, No. 12, pp. 1255-1258, 1987.
H. -J. Zeiss et al. "Enantioselective Synthesis of L-Phosphinothricin from L-Methionine and L-Glutamic Acid via L-Vinylglycine", Tetrahedron, vol. 48, No. 38, pp. 8263-8270, 1992.
H. -J. Zeiss et al. "Enantioselective Synthesis of Both Enantiomers of Phosphinothriacin via Asymmetric Hydrogenation of α-Acylamido Acrylates", J. Org. Chem. 1991, 56, 1783-1788.
W. Tang et al. "New Chiral Phosphorus Ligands for Enantioselective Hydrogenation", Chem. Rev. 2003, 103, 3029-3069.
M. J. Burk et al. "$C^2$-Symmetric Bis(phospholanes) and Their Use in Highly Enantioselective Hydrogenation Reactions", J. Am. Chem. Soc. 1991, 113, 8518-8519.
J. Holz et al. "Synthesis of a New Class of Functionalized Chiral Bisphospholane ligands and the Application in Enantioselective Hydrogenations", J. Org. Chem. 1988, 63, 8031-8034.
W. Li et al. "Synthesis of Chiral Hydroxyl Phospholanes from D-mannitol and Their Use in Asymmetric Catalytic Reactions", J. Org. Chem. 2000, 65 3489-3496.
U. Berens et al. "Chiral 1,1'-Diphosphetanylferrocenes: New Ligands for Asymetric Catalytic Hydrogenation of Itaconate Derivatives", Angew. Chem. Int. Ed. 2000, 39, No. 11, pp. 1981-1984.
J. Holz et al. "Synthesis of a New Chiral Bisphospholane Ligand for the Rh(I)-Catalyzed Enantioselective Hydrogenation of Isomeric β-Acylamido Acrylates", J. Org. Chem. 2003, 68, 1701-1707.
R. R. Schrock et al. "Coordinatively Unsaturated Cationic Complexes of Rhodium(I), Iridium(I), Palladium(II), and Platinum(II). Generation, Synthetic Utility, and Some Catalytic Studies", Journal of the American Chemical Society, vol. 93, No. 12, 1971, pp. 3089-3091.
B. D. Vineyard et al. "Asymmetric Hydrogenation. Rhodium Chiral Bisphophine Catalyst", Journal of the American Chemical Society, vol. 99, No. 18, 1977, pp. 5946-5952.

METHOD FOR PRODUCING L-2-AMINO-4-(HYDROXYMETHYL-PHOSPHINYL)-BUTANOIC ACID

TECHNICAL FIELD

This invention relates to a method for producing L-2-amino-4-(hydroxymethylphosphinyl)-butanoic acid (abbreviated as L-AMPB herein) which is useful as a herbicide.

BACKGROUND ART

D,L-2-amino-4-(hydroxymethylphosphinyl)-butanoic acid (abbreviated as DL-AMPB herein) is a well known compound having a herbicidal activity, and is used as an effective herbicide having a broad-spectrum (JP Patent Kokai JP-A-52-139727). However, it has been shown that the herbicidal activity of DL-AMPB is about one-half that of L-2-amino-4-(hydroxymethylphosphinyl)-butanoic acid (abbreviated as L-AMPB herein), and the essence of the activity is L-AMPB (JP Patent Kokai JP-A-55-000025, JP Patent Kokai JP-A-59-219297). Therefore, there is a strong desire to develop an efficient method for producing L-AMPB selectively.

Conventionally known methods for producing L-AMPB include (a) methods making use of microorganisms, enzymes, and (b) asymmetric synthesis methods. As the methods (a), there are disclosures such as a method for producing L-AMPB from 4-(hydroxymethylphosphinyl)-2-oxobutanoic acid with transaminase (JP Patent Kohyo JP-A-2003-528572) and a method for subjecting N-acetyl-DL-AMPB to enzymatic racemic resolution to produce L-AMPB (JP Patent Kohyo JP-A-2003-505031). However, in all of these methods, there are problems such that the reaction needs to be carried out at a low substrate concentration, complicated processes of aftertreatment and purification are required, and further an equimolar or more amount of expensive optically active amino acid(s) must be used in the transamination. There are disclosures, as the asymmetric synthesis methods (b), such as a method for alkylating (R)-3-isopropyl-2,5-dialkoxy-3,6-dihydropyrazine to synthesize L-AMPB (JP Patent Kokai JP-A-62-132891, and Tetrahedron Lett. 1255 (1987)) and a method for converting L-vinylglycine into L-AMPB stereospecifically (Tetrahedron Lett. 8263 (1992)). However, expensive optically active amino acids such as D-valine and L-vinylglycine need to be used for a starting material in these methods. Therefore, there are problems concerning inexpensive supply of raw material(s) in large quantities. Moreover, there are disclosed asymmetric synthesis methods such as a method for producing L-AMPB by subjecting 2-acetamide-4-(hydroxymethylphosphinyl)-butanoic acid to asymmetric hydrogenation reaction (JP Patent Kokai JP-A-62-226993, and J. Org. Chem. 56, 1783 (1991)). In this method, the asymmetric hydrogenation reaction is carried out using a rhodium catalyst comprising an optically active diphenylphosphine compound as a ligand. Therefore, it is thought that this method is efficient in terms of the use of chiral source in a catalytic amount. However, there is a problem such that optical yield is not high in this method.

On the other hand, asymmetric hydrogenation reaction to convert dehydroamino acid into amino acid using the rhodium catalyst in general is well known already (Chem. Rev., 103, 3029-3070 (2003)). However, most of the reactions are asymmetric reductions against dehydroamino acid having alkyl group and aryl group at side chain(s), and reactions using dehydroamino acid having highly polar substituent at side chain(s) are scarcely exemplified.

[Patent Publication 1] JP Patent Kokai JP-A-52-139727
[Patent Publication 2] JP Patent Kokai JP-A-55-000025
[Patent Publication 3] JP Patent Kokai JP-A-59-219297
[Patent Publication 4] JP Patent Kohyo JP-A-2003-505031
[Patent Publication 5] JP Patent Kokai JP-A-62-132891
[Patent Publication 6] JP Patent Kokai JP-A-62-226993
[Non-patent Document 1] Tetrahedron Lett. 1255 (1987)
[Non-patent Document 2] Tetrahedron 8263 (1992)
[Non-patent Document 3] J. Org. Chem. 56, 1783 (1991)
[Non-patent Document 4] Chem. Rev., 103, 3029-3070 (2003)

DISCLOSURE OF THE INVENTION

Problem to be Solved by the Invention

It is an object of the present invention to provide an efficient method for producing L-AMPB, which is useful as a herbicide, in high enantiomeric excess through catalytic asymmetric synthesis reaction.

Means to Solve the Problem

The present inventors have conducted studies on asymmetric catalysts in asymmetric hydrogenation reaction of 2-acetylamide-4-(hydroxymethylphosphinyl)-butanoic acid and, as a result, found that L-AMPB is efficiently obtained in a high enantiomeric excess in case of using a rhodium catalyst having an optically active cyclic phosphine ligand. This finding has led to the completion of the present invention.

That is, the present invention is set forth as follows.

A method for producing L-2-amino-4-(hydroxymethylphosphinyl)-butanoic acid represented by the following formula (5):

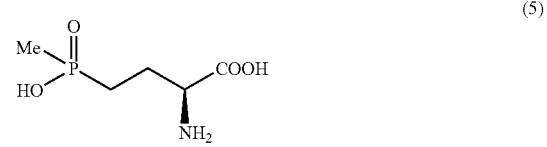

(5)

comprising the steps of:
subjecting a compound represented by the following formula (1):

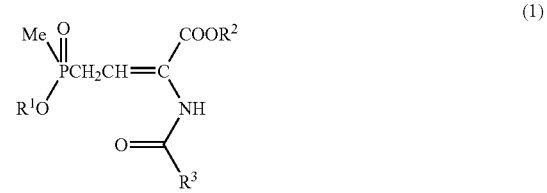

(1)

[where $R^1$ and $R^2$ represent identically or differently hydrogen atom or $C_{1-4}$ alkyl group, and $R^3$ represents $C_{1-4}$ alkyl group, aryl group, $C_{1-4}$ alkyloxy group or aryloxy group]

to hydrogenation reaction under hydrogen atmosphere in the presence of asymmetric catalyst to produce a compound represented by the following formula (4):

(4)

[chemical structure: phosphorus compound with Me, R¹O, P=O, connected to CH chain with COOR² and NH-C(=O)-R³]

[where $R^1$, $R^2$ and $R^3$ have the same meaning as the formula (1)];

and subjecting the produced compound represented by the formula (4) to hydrolysis;

said asymmetric catalyst being represented by the following formula (2):

$$[Rh(R^4)(L)]X \quad (2)$$

[where $R^4$ represents 1,5-cyclooctadiene or norbornadiene, L represents an optically active cyclic phosphine ligand represented by the following formula (6) or (8), and X represents $BF_4$, $ClO_4$, $PF_6$, $SbF_6$, $BPh_4$, or OTf (where Tf represents trifluoromethanesulfonyl group)]

or the following formula (3):

$$[Rh(L)(Z)]_2 \quad (3)$$

[where L has the same meaning as in the formula (2), and Z represents halogen atom];

said formula (6) being:

(6)

[chemical structure showing phospholane ligand with substituents $R^5$, $R^6$, $R^7$, $R^8$ and bridging group Y between two P atoms]

[where $R^5$ and $R^8$ represent $C_{1-4}$ alkyl group, and $R^6$ and $R^7$ represent hydrogen atom or hydroxyl group, and Y represents a group selected from the groups represented by the following formula (7):

(7)

[structures: ortho-xylylene, —CH$_2$CH$_2$—, N-methylmaleimide-like, maleic anhydride-like, methylbenzothiophene-like]

[where Me represents methyl group]];

said formula (8) being (8)

[ferrocene-based bisphosphetane structure with $R^9$ and $R^{10}$ substituents, Fe center]

[where $R^9$ and $R^{10}$ represent $C_{1-4}$ alkyl group].

Moreover, in one preferred embodiment of the present invention, L in the formula (2) or (3) can be a ligand represented by the formula (8), and, in another preferred embodiment of the present invention, L in the formula (2) or (3) can be a ligand represented by the formula (6).

In a further preferred embodiment of the present invention, L can be 1,2-bis(2,5-dimethyl phosphorano) benzene, 1,2-bis(2,5-diethyl phosphorano) benzene, 1,2-bis(2,5-diisopropyl phosphorano) benzene, 1,2-bis(2,5-dimethyl-3,4-dihydroxy-phosphorano) benzene, 1,2-bis(2,5-dimethyl phosphorano) ethane, or 1,2-bis(2,5-diethyl phosphorano) ethane.

In a preferred embodiment of the present invention, the asymmetric catalyst represented by the formula (2) can be used.

In a preferred embodiment of the present invention, the asymmetric catalyst represented by the formula (2) can be used, and L in the formula (2) can be a ligand represented by the formula (6).

In a preferred embodiment of the present invention, L in the formula (2) or (3) can be a ligand represented by the formula (6), and Y in the ligand represented by the formula (6) can be a group selected from the groups represented by the following formula (9):

(9)

[ortho-xylylene structure], —CH$_2$CH$_2$—

In a further preferred embodiment of the present invention, L can be 1,2-bis(2,5-dimethyl phosphorano) benzene, 1,2-bis(2,5-diethyl phosphorano) benzene, 1,2-bis(2,5-diisopropyl phosphorano) benzene, 1,2-bis(2,5-dimethyl-3,4-dihydroxy-phosphorano) benzene, 1,2-bis(2,5-dimethyl phosphorano) ethane, or 1,2-bis(2,5-diethyl phosphorano) ethane.

In a preferred embodiment of the present invention, the asymmetric catalyst represented by the formula (2), wherein X is OTf or $BF_4$, can be used.

In a preferred embodiment of the present invention, $R^1$ and $R^2$ can be hydrogen atom and $R^3$ can be $C_{1-4}$ alkyl group, in the formula (1).

EFFECT OF THE INVENTION

According to the method of the present invention, L-AMPB, which is useful as a herbicide, can be efficiently produced in high enantiomeric excess, 92% ee or more.

PREFERRED MODE(S) FOR CARRYING OUT THE INVENTION

The groups represented by $R^1$, $R^2$ and $R^3$ in the compounds represented by the formulae (1) and (4) used in the present invention are explained.

$C_{1-4}$ alkyl groups represented by $R^1$, $R^2$ and $R^3$ or $C_{1-4}$ alkyl groups existing on the substituent represented by $R^1$, $R^2$ and $R^3$ are specifically exemplified by methyl group, ethyl group, n-propyl group, isopropyl group, n-butyl group, 2-butyl group, isobutyl group, and t-butyl group.

Aryl groups represented by $R^1$, $R^2$ and $R^3$ or aryl groups on the groups represented by $R^1$, $R^2$ and $R^3$ are specifically exemplified by phenyl group, naphthyl group, and anthracenyl group.

The compound represented by the formula (1) can be synthesized by the method described in JP Patent Kokai JP-A-62-226993 or J. Org. Chem. 56, 1783 (1991).

In the compound represented by the formula (1), it is preferable that $R^1$ and $R^2$ are hydrogen atom, and $R^3$ is $C_{1-4}$ alkyl group.

Concrete examples of the compounds represented by the formula (1) include the following compounds:
2-acetamide-4-(hydroxymethylphosphinyl)-butenoic acid,
2-propionylamide-4-(hydroxymethylphosphinyl)-butenoic acid,
2-benzoylamide-4-(hydroxymethylphosphinyl)-butenoic acid,
2-t-butoxycarbonylamide-4-(hydroxymethylphosphinyl)-butenoic acid,
2-benzyloxycarbonylamide-4-(hydroxymethylphosphinyl)-butenoic acid,
2-acetamide-4-(methoxy(methyl)phosphinyl)-butenoic acid methyl ester,
2-propionylamide-4-(methoxy(methyl)phosphinyl)-butenoic acid methyl ester,
2-benzoylamide-4-(methoxy(methyl)phosphinyl)-butenoic acid methyl ester,
2-t-butoxycarbonylamide-4-(methoxy(methyl)phosphinyl)-butenoic acid methyl ester,
2-benzyloxycarbonylamide-4-(methoxy(methyl)phosphinyl)-butenoic acid methyl ester,
2-acetamide-4-(methoxy(methyl)phosphinyl)-butenoic acid methyl ester,
2-propionylamide-4-(methoxy(methyl)phosphinyl)-butenoic acid,
2-benzoylamide-4-(methoxy(methyl)phosphinyl)-butenoic acid,
2-t-butoxycarbonylamide-4-(methoxy(methyl)phosphinyl)-butenoic acid,
2-benzyloxycarbonylamide-4-(methoxy(methyl)phosphinyl)-butenoic acid,
2-acetamide-4-(hydroxymethylphosphinyl)-butenoic acid methyl ester,
2-propionylamide-4-(hydroxymethylphosphinyl)-butenoic acid methyl ester,
2-benzoylamide-4-(hydroxymethylphosphinyl)-butenoic acid methyl ester,
2-t-butoxycarbonylamide-4-(hydroxymethylphosphinyl)-butenoic acid methyl ester, and
2-benzyloxycarbonylamide-4-(hydroxymethylphosphinyl)-butenoic acid methyl ester.

The groups represented by $R^5$, $R^8$, $R^9$, $R^{10}$, and Z in the asymmetric catalysts represented by the formulae (2) and (3) used in the present invention are explained.

$C_{1-4}$ alkyl groups represented by $R^5$, $R^8$, $R^9$ and $R^{10}$ are concretely exemplified by methyl group, ethyl group, n-propyl group, isopropyl group, n-butyl group, 2-butyl group, isobutyl group, and t-butyl group.

Halogen atoms represented by Z are concretely exemplified by chlorine atom, bromine atom, and iodine atom.

With respect to a combination(s) of $R^5$, $R^6$, $R^7$, and $R^8$ in the ligand represented by the formula (6) used in the present invention, it is preferable that $R^5$ and $R^8$ are $C_{1-4}$ alkyl group, and $R^6$ and $R^7$ are hydrogen atom; or $R^5$ and $R^8$ are $C_{1-4}$ alkyl group, and $R^6$ and $R^7$ are hydroxy group.

Moreover, the asymmetric ligand represented by L can be synthesized by the method described in J. Am. Chem. Soc., 113, 8518 (1991), J. Org. Chem., 63, 8031 (1998), J. Org. Chem. 65, 3489 (2000), Angew. Chem. Int. Ed. 39, 1981 (2000), or J. Org. Chem. 68, 1701 (2003), or is commercially available.

L is, preferably, a ligand represented by the formula (6) or (8), more preferably, a ligand represented by the formula (6). Further, Y is preferably a group selected from the groups represented by the formula (9). Especially preferably, L is exemplified by the ligand represented by the formula (6), wherein Y is phenyl group, and $R^5$ and $R^8$ are $C_{1-4}$ alkyl group, and $R^6$ and $R^7$ are hydrogen atom.

Concrete examples of L include, for example, 1,2-bis(2,5-dimethyl phosphorano) benzene, 1,2-bis(2,5-diethyl phosphorano) benzene, 1,2-bis(2,5-diisopropyl phosphorano) benzene, 1,2-bis(2,5-dimethyl-3,4-dihydroxy phosphorano) benzene, 1,2-bis(2,5-dimethyl phosphorano) ethane, 1,2-bis(2,5-diethyl phosphorano) ethane, 1,1'-bis(2,4-dimethyl phosphothano) ferrocene, 1,1'-bis(2,4-diethyl phosphothano) ferrocene, 2,3-bis(2,5-dimethyl phosphoranyl)maleic anhydride, 2,3-bis(2,5-dimethyl phosphoranyl) maleic-N-methylimide, 2,3-bis(2,5-dimethyl phosphorano) benzo[b]thiophene, and 2,3-bis(2,5-diethyl phosphorano) benzo[b]thiophene, etc. Preferably, 1,2-bis(2,5-dimethyl phosphorano) benzene, 1,2-bis(2,5-diethyl phosphorano) benzene, 1,2-bis(2,5-diisopropyl phosphorano) benzene, 1,2-bis(2,5-dimethyl-3,4-dihydroxy phosphorano) benzene, 1,2-bis(2,5-dimethyl phosphorano) ethane, or 1,2-bis(2,5-diethyl phosphorano) ethane is selected. More concrete examples of L include (S,S)-1,2-bis(2,5-dimethyl phosphorano) benzene (abbreviated as (S,S)-Me-DUPHOS™), (S,S)-1,2-bis(2,5-diethyl phosphorano) benzene (abbreviated as (S,S)-Et-DUPHOS™), (R,R)-1,2-bis(2,5-diisopropyl phosphorano) benzene (abbreviated as (R,R)-iPr-DUPHOS™), (S,S,S,S)-1,2-bis(2,5-dimethyl-3,4-dihydroxy phosphorano) benzene (abbreviated as (S,S,S,S)-ROPHOS®), (S,S)-1,2-bis(2,5-dimethyl phosphorano) ethane (abbreviated as (S,S)-Me-BPE), (S,S)-1,2-bis(2,5-diethyl phosphorano) ethane (abbreviated as (S,S)-Et-BPE), 1,1'-bis(2,4-dimethyl phosphothano) ferrocene (abbreviated as Me-FerroTANE®), (S,S)-1,1'-bis(2,4-diethyl phosphothano) ferrocene (abbreviated as (S,S)-Et-FerroTANE®), (S,S)-2,3-bis(2,5-dimethyl phosphoranyl) maleic anhydride, (S,S)-2,3-bis(2,5-dimethyl phosphoranyl) maleic-N-methylimide, (S,S)-2,3-bis(2,5-dimethyl phosphorano) benzo[b]thiophene, and (S,S)-2,3-bis(2,5-diethyl phosphorano) benzo[b]thiophene. Preferably, (S,S)-Me-DUPHOS™, (S,S)-Et-DUPHOS™, (R,R)-iPr-DUPHOS™, (S,S,S,S)-ROPHOS®, (S,S)-Me-BPE, or (S,S)-Et-BPE is selected.

The asymmetric catalysts represented by the formulae (2) and (3) can be synthesized by the method described in J. Am. Chem. Soc., 93, 3089 (1971), J. Am. Chem. Soc., 99, 5946 (1977), Chemical Society of Japan, "JIKKEN KAGAKU KOZA (Course of Study of Experimental Chemical) 4th ed.", Organic metallic complex, 18, 339-344 (1991) Maruzen, or can be purchased from a market.

With respect to the asymmetric catalyst, the compound represented by the formula (2) is preferably used.

The asymmetric catalyst represented by the formula (2) or (3) is concretely exemplified by [Rh(L)Cl]$_2$, [Rh(L)Br]$_2$, [Rh(L)I]$_2$, [Rh(cod)L]BF$_4$, [Rh(cod)L]OTf, [Rh(cod)L]BPh$_4$, [Rh(cod)L]ClO$_4$, [Rh(cod)L]PF$_6$, [Rh(nbd)L]BF$_4$, [Rh(nbd)L]OTf, [Rh(nbd)L]BPh$_4$, [Rh(nbd)L]ClO$_4$, and [Rh(nbd)L]PF$_6$, etc. More preferably, [Rh(cod)L]BF$_4$, [Rh(cod)L]OTf, [Rh(nbd)L]BF$_4$, or [Rh(nbd)L]OTf is selected (in this case where, especially preferably, L is exemplified by the ligand represented by the formula (6), wherein Y is phenyl group, R$^5$ and R$^8$ are C$_{1-4}$ alkyl group, and R$^6$ and R$^7$ are hydrogen atom). Here, cod and nbd represent 1,5-cyclooctadiene and norbornadiene, respectively.

In the method of subjecting the compound represented by the formula (1) to hydrogenation reaction using the asymmetric catalyst represented by the formula (2) or (3), to produce the compound represented by the formula (4), solvents to be used are exemplified by methanol, ethanol, n-propanol, isopropanol, n-butanol, s-butanol, t-butanol, n-pentanol, methoxyethanol, trifluoroethanol, diethylether, tetrahydrofuran, dimethoxyethane, dioxane, water, methylene chloride, chloroform, benzene, toluene, acetone, acetonitrile, N,N-dimethylformamide, dimethylsulfoxide and a combination(s) of two or more kinds of these solvents. Preferably, methanol, ethanol, n-propanol, n-butanol, n-pentanol, water or a combination of two or more kinds of these solvents is selected. The reaction concentration is selected within the range of from 1 to 60% by mass, preferably from 5 to 40% by mass. The amount of use of asymmetric catalyst is selected such that the ratio of the compound represented by the formula (1)/asymmetric catalyst represented by the formula (2) or (3) in molar ratio is within the range of from 10 to 100000, preferably from 100 to 10000. The reaction temperature is selected within the range of from 0 to 100° C., preferably from 15 to 60° C. The hydrogen pressure is selected within the range of from a hydrogen atmosphere to 100 atmospheres, preferably from 1 to 10 atmospheres. The reaction time differs depending on the sort or the used amount of the catalyst. The reaction time is ordinarily selected within the range of from 1 minute to 48 hours, preferably from 10 minutes to 24 hours.

In the reaction of subjecting the compound represented by the formula (4) to hydrolysis to produce the compound represented by the formula (5), solvents to be used are exemplified by water, and acids to be used are exemplified by mineral acids such as hydrochloric acid and sulfuric acid. The concentration in case of using hydrochloric acid is ordinarily selected within the range of from 6 to 12M, and the concentration in case of using sulfuric acid is ordinarily selected within the range of from 2 to 18M. The reaction temperature is selected within the range of from 20 to 150° C., preferably from 50 to 120° C. The reaction time is selected within the range of from 2 to 12 hours, preferably from 4 to 8 hours.

EXAMPLES

Hereinafter, the present invention is concretely explained by referring to Examples. However, the present invention is not limited to these Examples.

In the following Examples, (+)-1,2-bis((2S,5S)-2,5-dimethyl phosphorano benzene(cyclooctadiene)rhodium(I) trifluoromethanesulfonate is abbreviated as [Rh((S,S)-Me-DUPHOS™)(cod)]OTf, and (+)-1,2-bis((2S, 5S)-2,5-diethyl phosphorano benzene(cyclooctadiene)rhodium(I) trifluoromethanesulfonate is abbreviated as [Rh((S,S)-Et-DUPHOS™)(cod)]OTf, and bis(1,5-cyclooctadiene)rhodium(I) trifluoromethanesulfonate is abbreviated as [Rh(cod)$_2$]OTf, and (−)-1,2-bis((2S,5S)-2,5-diisopropyl phosphorano benzene is abbreviated as (S,S)-iPr-DUPHOS™, and (+)-1,2-bis((2S, 5S)-2,5-dimethyl-(3S,4S)-3,4-dihydroxy phosphorano)benzene bis(trifluoromethanesulfonate) is abbreviated as (S, S, S, S)-ROPHOS®-bis(OTf), and (−)-1,1'-bis((2S, 4S)-2,4-diethyl phosphothano)ferrocene(1,5-cyclooctadiene)rhodium(I) tetrafluoroborate is abbreviated as [Rh((S,S)-Et-FerroTANE®)(cod)]BF$_4$. Here, [Rh((S,S)-Me-DUPHOS™)(cod)]OTf, [Rh((S,S)-Et-DUPHOS™)(cod)]OTf, [Rh(cod)$_2$]OTf, (S,S)-iPr-DUPHOS™, (S,S,S,S)-ROPHOS®-bis(OTf) and [Rh((S,S)-Et-FerroTANE®)(cod)]BF$_4$, which are manufactured by Strem Co., were used.

Determination of Enantiomeric Excess

The enantiomeric excess for the produced compound (5) was determined using high performance liquid chromatography (HPLC) under the following conditions. The D-form is firstly eluted, and the L-form is secondly eluted.
Column: SUMICHIRAL OA6100 (4.6×150 mm),
Mobile phase: 2 mM copper sulfate aqueous solution
Detection: UV254 nm
Flow rate: 1.0 ml/min
Column temperature: 30° C.

Example 1

Production of
L-2-amino-4-(hydroxymethylphosphinyl)-butanoic acid 300 mg of 2-acetamino-4-(hydroxymethylphosphinyl)-butanoic acid, 9.0 mg of [Rh((S,S)-Me-DUPHOS™)(cod)]OTf, and 10 ml of methanol were put in a stainless autoclave under argon atmosphere, and then stirred at room temperature for 22 hours under a hydrogen pressure of 0.3 MPa. After the conclusion of the reaction, the solvent was concentrated under reduced pressure, and to the residue thus obtained was added 10 ml of 6N hydrochloric acid, and the mixture thus obtained was refluxed for 12 hours. The solvent was distilled away under reduced pressure, and 4 ml of propyleneoxide was added, and the mixture thus obtained was stirred for 1 hour. After the concentration under reduced pressure, the residue thus obtained was purified with ion-exchange resin (Dowex® 1×4 Ac, 200-400 mesh: eluent 10% acetic acid aqueous solution) to obtain 211 mg of objective L-2-amino-4-(hydroxymethylphosphinyl)-butanoic acid as a solid. HPLC analysis (retention time: D-form 4.0 minutes, L-form 5.5 minutes) indicated that the enantiomeric excess of this product was 92.9% ee.
$^1$H-NMR (D$_2$O) δ: 1.28 (3H, d, J=13.9 Hz), 1.57-1.78 (2H, m), 1.95-2.11 (2H, m), 3.89 (1H, t, J=6.1 Hz)
APIMASS: m/z 182[M+H]$^+$..

Example 2

Production of L-2-amino-4-(hydroxymethylphosphinyl)-butanoic acid

When the reaction was carried out in the same manner as in Example 1 except that 10 ml of n-butanol was used as a solvent instead of 10 ml of methanol in Example 1, 215 mg of objective L-2-amino-4-(hydroxymethylphosphinyl)-butanoic acid was obtained. HPLC analysis indicated that the enantiomeric excess of this product was 92.7% ee.

Example 3

Production of L-2-amino-4-(hydroxymethylphosphinyl)-butanoic acid

When the reaction was carried out in the same manner as in Example 1 except that 9.8 mg of [Rh((S,S)-Et-DUPHOS™)(cod)]OTf was used as a catalyst instead of 9.0 mg of [Rh((S,S)-Me-DUPHOS™)(cod)]OTf in Example 1 and 10 ml of n-butanol was used as a solvent instead of 10 ml of methanol, 180 mg of objective L-2-amino-4-(hydroxymethylphosphinyl)-butanoic acid was obtained. HPLC analysis indicated that the enantiomeric excess of this product was 95.6% ee.

Example 4

Production of D-2-amino-4-(hydroxymethylphosphinyl)-butanoic acid

When the reaction was carried out in the same manner as in Example 1 except that 6.4 mg of [Rh(cod)$_2$]OTf and 5.7 mg of (S,S)-iPr-DUPHOS™ were used as a catalyst instead of 9.0 mg of [Rh((S,S)-Me-DUPHOS™)(cod)]OTf in Example 1 and 10 ml of n-propanol was used as a solvent instead of 10 ml of methanol, 218 mg of objective D-2-amino-4-(hydroxymethylphosphinyl)-butanoic acid was obtained. HPLC analysis indicated that the enantiomeric excess of this product was 93.6% ee.

Example 5

Production of L-2-amino-4-(hydroxymethylphosphinyl)-butanoic acid

When the reaction was carried out in the same manner as in Example 1 except that 6.4 mg of [Rh(cod)$_2$]OTf and 9.1 mg of (S,S,S,S)-ROPHOS®-bis(OTf) were used as a catalyst instead of 9.0 mg of [Rh((S,S)-Me-DUPHOS™)(cod)]OTf in Example 1 and 27.5 mg of triethylamine was added as an additive with a reaction time being from 22 to 44 hours, 190 mg of objective L-2-amino-4-(hydroxymethylphosphinyl)-butanoic acid was obtained. HPLC analysis indicated that the enantiomeric excess of this product was 92.4% ee.

Example 6

Production of L-2-amino-4-(hydroxymethylphosphinyl)-butanoic acid

When the reaction was carried out in the same manner as in Example 1 except that 10.1 mg of [Rh((S,S)-Et-FerroTANE®)(cod)]BF$_4$ was used as a catalyst instead of 9.0 mg of [Rh((S,S)-Me-DUPHOS™)(cod)]OTf in Example 1 and 10 ml of n-propanol was used as a solvent instead of 10 ml of methanol, 221 mg of objective L-2-amino-4-(hydroxymethylphosphinyl)-butanoic acid was obtained. HPLC analysis indicated that the enantiomeric excess of this product was 92.0% ee.

Example 7

Production of L-2-amino-4-(hydroxymethylphosphinyl)-butanoic acid

When the reaction was carried out in the same manner as in Example 1 except that 340 mg of methyl 2-acetamino-4-(methoxy(methyl)phosphinyl)-butenoate was used as a raw material instead of 300 mg of 2-acetamino-4-(hydroxymethylphosphinyl)-butenoic acid in Example 1 and 9.8 mg of [Rh((S,S)-Et-DUPHOS™)(cod)]OTf was used as a catalyst instead of 9.0 mg of [Rh((S,S)-Me-DUPHOS™)(cod)]OTf, 159 mg of objective L-2-amino-4-(hydroxymethylphosphinyl)-butanoic acid was obtained. HPLC analysis indicated that the enantiomeric excess of this product was 92.1% ee.

INDUSTRIAL APPLICABILITY

In the method of the present invention, a compound represented by the formula (1) is subjected to asymmetric hydrogenation reaction using a rhodium catalyst having an optically active cyclic phosphine ligand to synthesize L-AMPB selectively. Therefore, the method of the present invention is an excellent method for synthesizing an optically active substance inexpensively, effectively, and high-selectively as compared to the conventional methods for synthesizing the optically active substance.

The invention claimed is:

1. A method for producing L-2-amino-4-(hydroxymethylphosphinyl)-butanoic acid represented by formula (5):

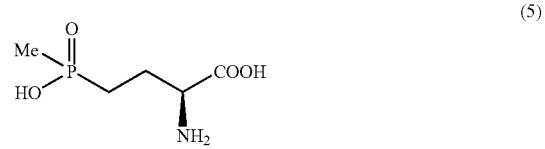

(5)

comprising:
subjecting a compound represented by formula (1):

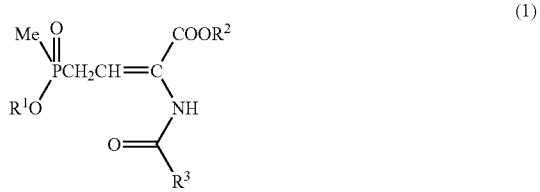

(1)

wherein R¹ and R² represent, identically or differently, a hydrogen atom or a $C_{1-4}$ alkyl group, and R³ represents a $C_{1-4}$ alkyl group, an aryl group, a $C_{1-4}$ alkyloxy group, or an aryloxy group, to a hydrogenation reaction under a hydrogen atmosphere in the presence of an asymmetric catalyst to produce a compound represented by formula (4):

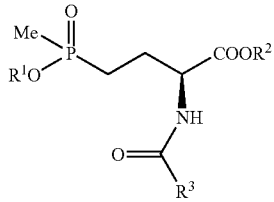

(4)

wherein R¹, R², and R³ have the same meaning as in formula (1); and subjecting the produced compound represented by formula (4) to hydrolysis;

said asymmetric catalyst being represented by formula (2):

(2)

wherein R⁴ represents 1,5-cyclooctadiene or norbornadiene, L represents an optically active cyclic phosphine ligand represented by formula (6) or (8), and X represents $BF_4$, $ClO_4$, $PF_6$, $SbF_6$, $BPh_4$, or OTf wherein Tf represents a trifluoromethanesulfonyl group;

or formula (3):

(3)

wherein L has the same meaning as in formula (2), and Z represents a halogen atom;

said formula (6) being:

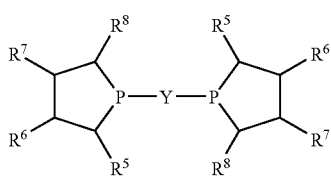

(6)

wherein R⁵ and R⁸ represent $C_{1-4}$ alkyl groups, and R⁶ and R⁷ represent a hydrogen atom, and Y represents a group selected from the groups represented by formula (9):

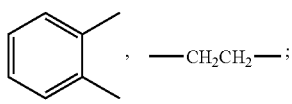

(9)

said formula (8) being

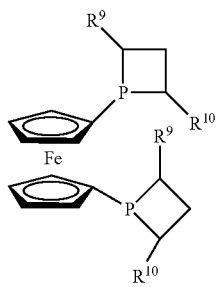

(8)

wherein R⁹ and R¹⁰ represent $C_{1-4}$ alkyl groups.

2. The method according to claim 1, wherein L in formula (2) or (3) is a ligand represented by the formula (8).

3. The method according to claim 1, wherein L in formula (2) or (3) is a ligand represented by formula (6).

4. The method according to claim 1, wherein the asymmetric catalyst represented by formula (2) is used.

5. The method according to claim 1, wherein the asymmetric catalyst represented by formula (2) is used and L in formula (2) is a ligand represented by formula (6).

6. The method according to claim 1, wherein in the asymmetric catalyst represented by formula (2), X is OTf or $BF_4$.

7. The method according to claim 1, wherein in formula (1), R¹ and R² are hydrogen atoms and R³ is a $C_{1-4}$ alkyl group.

8. The method according to claim 1, wherein L is 1,2-bis (2,5-dimethyl phosphorano) benzene; 1,2-bis(2,5-diethyl phosphorano) benzene; 1,2-bis(2,5-diisopropyl phosphorano) benzene; 1,2-bis(2,5-dimethyl phosphorano) ethane; or 1,2-bis(2,5-diethyl phosphorano) ethane.

9. The method according to claim 2, wherein in the asymmetric catalyst represented by formula (2), X is OTf or $BF_4$.

10. The method according to claim 3, wherein in the asymmetric catalyst represented by formula (2), X is OTf or $BF_4$.

11. The method according to claim 4, wherein in the asymmetric catalyst represented by formula (2), X is OTf or $BF_4$.

12. The method according to claim 5, wherein in the asymmetric catalyst represented by formula (2), X is OTf or $BF_4$.

13. The method according to claim 2, wherein in the formula (1), R¹ and R² are hydrogen atoms and R³ is a $C_{1-4}$ alkyl group.

14. The method according to claim 3, wherein in the formula (1), R¹ and R² are hydrogen atoms and R³ is a $C_{1-4}$ alkyl group.

15. The method according to claim 4, wherein in the formula (1), R¹ and R² are hydrogen atoms and R³ is a $C_{1-4}$ alkyl group.

16. The method according to claim 5, wherein in the formula (1), R¹ and R² are hydrogen atoms and R³ is a $C_{1-4}$ alkyl group.

17. The method according to claim 6, wherein in the formula (1), R¹ and R² are hydrogen atoms and R³ is a $C_{1-4}$ alkyl group.

18. A method for producing L-2-amino-4-(hydroxymethylphosphinyl)-butanoic acid represented by formula (5):

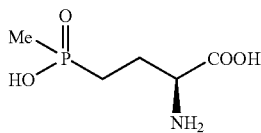

comprising:
subjecting a compound represented by formula (1):

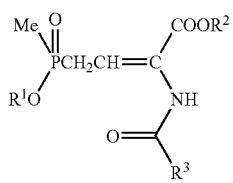

wherein $R^1$ and $R^2$ represent, identically or differently, a hydrogen atom or a $C_{1-4}$ alkyl group, and $R^3$ represents a $C_{1-4}$ alkyl group, an aryl group, a $C_{1-4}$ alkyloxy group, or an aryloxy group,
to a hydrogenation reaction under a hydrogen atmosphere in the presence of an asymmetric catalyst to produce a compound represented by formula (4):

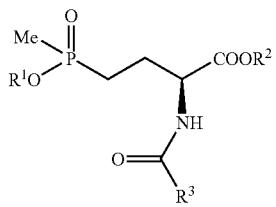

wherein $R^1$, $R^2$, and $R^3$ have the same meaning as in formula (1); and
subjecting the produced compound represented by formula (4) to hydrolysis;
said asymmetric catalyst being represented by formula (2):

$$[Rh(R^4)(L)]X \quad (2)$$

wherein $R^4$ represents 1,5-cyclooctadiene or norbornadiene, L represents an optically active cyclic phosphine ligand represented by formula (6), and X represents $BF_4$, $ClO_4$, $PF_6$, $SbF_6$, $BPh_4$, or OTf wherein Tf represents a trifluoromethanesulfonyl group;
or formula (3):

$$[Rh(L)(Z)]_2 \quad (3)$$

wherein L has the same meaning as in formula (2), and Z represents a halogen atom;
said formula (6) being:

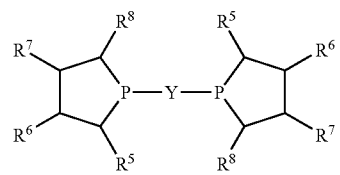

wherein $R^5$ and $R^8$ represent $C_{1-4}$ alkyl groups, and $R^6$ and $R^7$ represent a hydrogen atom, and Y represents:

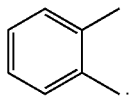

* * * * *